United States Patent [19]

Nandagiri et al.

[11] Patent Number: 5,382,426
[45] Date of Patent: Jan. 17, 1995

[54] CYSTEAMINE PERMAMENT WAVE COMPOSITION AND METHOD

[75] Inventors: Arun Nandagiri, Libertyville; Richard A. Abbott, Westmont; Renee E. Nardone, Chicago, all of Ill.; Edward T. Borish, Mahwah, N.J.

[73] Assignee: Helene Curtis, Inc., Chicago, Ill.

[21] Appl. No.: 96,364

[22] Filed: Jul. 22, 1993

Related U.S. Application Data

[62] Division of Ser. No. 819,113, Jan. 10, 1992, Pat. No. 5,260,054.

[51] Int. Cl.$^6$ .............. A61K 7/06; A61K 7/11; A45D 2/12; A45D 7/04
[52] U.S. Cl. .............. 424/70.51; 132/204; 132/210; 132/226
[58] Field of Search .............. 424/70, 71, 72; 132/204, 210, 226

[56] References Cited

U.S. PATENT DOCUMENTS 2,577,710 12/1951 McDonough ............ 133/7
2,577,711 12/1951 McDonough ............ 132/7
4,795,629 1/1989 Siuta-Mangano ........ 424/70
4,859,459 8/1989 Greiche et al. ......... 424/72
5,208,014 5/1993 Dubief et al. ......... 424/71

Primary Examiner—Thurman K. Page
Assistant Examiner—Carlos Azpuru
Attorney, Agent, or Firm—Marshall, O'Toole, Gerstein, Murray & Borun

[57] ABSTRACT

A single formula, mild permanent wave reducing composition and method of permanently waving or reshaping human hair that provides a strong, long lasting curl and leaves the hair soft while minimizing further damage to already damaged hair. The composition contains a cysteamine reducing agent compound selected from the group consisting of cysteamine, a cysteamine salt, and mixtures thereof. The cysteamine compound should be present in an amount of about 7.8% to about 9.0% by weight; and sufficient additional alkali, if necessary, to bring the pH of the composition to about 7.8 to about 8.5. Optionally, a hair softening and/or moisturizing agent, such as glycerine is included in the composition in an amount of about 0.1% to about 15% by weight of the composition.

21 Claims, 3 Drawing Sheets

CYSTEAMINE PERMAMENT WAVE COMPOSITION AND METHOD

CROSS REFERENCE TO RELATED APPLICATION

This application is a divisional of co-pending application Ser. No. 07/819,113, filed Jan. 10, 1934 now U.S. Pat. No. 5,260,054.

FIELD OF THE INVENTION

The present invention is directed to a cysteamine-based composition and method for relatively permanently reshaping or curling human hair into a lasting curl pattern. More particularly, the present invention is directed to a composition and method capable of forming a "permanent" wave in human hair such that regardless of the condition of the hair, i.e., whether it be substantially undamaged or normal hair, tinted hair, frosted hair, bleached hair or hair substantially damaged as a result of some other prior hair treatment or environmental condition, the composition will permanently reshape both normal and damaged hair to substantially the same extent without the danger of overprocessing. Significantly, the composition does not require a compound added for the purpose of establishing an equilibrium reaction with the reducing agent, e.g., a dithioglycolate, such as diammonium dithioglycolate, to prevent overprocessing of and damage to the hair. Further, the composition can be applied repeatedly to the hair without significant damage so that the hair can be permed at least every 3 to 6 weeks to maintain a fresh looking perm without significant damage.

BACKGROUND OF THE INVENTION

In general, permanent waving of human hair is achieved by chemically breaking the sulfur to sulfur or disulfide cystine bonds occurring naturally in human hair and then reforming the cystine bonds while the hair is wrapped or curled on rods. The sulfur to sulfur cystine bonds in human hair maintain the hair in a naturally straight or curly configuration and, in order to permanently reshape the hair into a lasting, different configuration, a significant percentage of the sulfur to sulfur bonds must be broken and then reestablished after the hair is reconfigured in a desired position, such as wrapped around a suitable mandrel or roller. In general, the sulfur to sulfur cystine bonds are broken with a composition containing a reducing agent and after the hair is wound into a curl formation around a rod or roller, the sulfur to sulfur cystine bonds are relinked or reestablished while the hair is in the curl formation by contacting the hair in the new formation with an oxidizing agent, such as hydrogen peroxide or a water-soluble bromate.

As set forth in German Offen. DE 3,631,991, others have used a reducing agent composition that is a combination of cysteamine, or its salts, together with a monothioglycolic acid ester for permanent hair waving (see CA Selects: Cosmetic Chemicals, Issue 1, 1989, 109: 236730h). Also an N-acylcysteamine HSCH$_2$CH$_2$NH—COR(R=2-10 C alkyl), as a hair reducing compound, has been used together with another reducing agent selected from the group consisting of cysteine, acidic sodium hyposulfite, sodium sulfite, thioglycerol and thiolactic acid, as disclosed in Japanese Patent JP63146808. Similarly, published European Patent Application 88306449.5, publication number 0299764, discloses the use of cysteamine as a reducing agent together with sulfite, bisulfite and disulfide compounds, such as cystamine, to effect reoxidation. The use of cystamine, as an oxidizing agent in the permanent waving process, is disclosed in Siuta-Mangano U.S. Pat. No. 4,795,629. Japanese published Patent Application No. 2053-714-A discloses cysteamine together with a dithioglycolate stop action compound.

The reducing action of mercaptans on keratin is due mostly to the dissociated form of the thiol groups, the thiolate anion. Acid permanent waves sufficiently curl hair at a lower pH compared to alkaline permanents because the waving agents in these permanents have low pKa values and thus exist predominantly in dissociated (thiolate) form at a pH near neutral, or slightly acidic pH. Hence, the pKa value shows that some mercaptans are efficient at high pH while others with a low pKa value and high ionization constant are efficient at lower pH values. For example, it is well known that the alkaline salts of thioglycolic acid, e.g., the ammonium salt of thioglycolic acid (pKa=10.4) has acceptable waving efficiency only if the pH of solution exceeds 9, see Zviak, Charles, The Science of Hair Care, Permanent Waving and Hair Straightening, p. 191, 1986; while amides such as thioglycolamide (pKa=8.4), and esters such as glycerol thioglycolate (pKa=7.8) give acceptable waving efficiency at neutral and even slightly acid pH.

The cysteamine-based reducing agent-containing composition and method of the present invention preferably do not include a compound selected from the group consisting of a monothioglycolate; a dithioglycolate; a monothioglyolic acid ester, e.g., thioglycerol; a thiolactic acid; a sulfite; and a hyposulfite, yet is unexpectedly effective in the pH range of about 7.8 to about 8.5 and particularly in the pH range of about 8.0 to 8.3.

Different reducing agents are effective to break the cystine bonds that cross link human hair protein at the different pHs. Generally speaking, the acid permanent wave compositions having a lower pH include reducing agents such as bisulfites, e.g., ammonium bisulfite, or glycerol monothioglycolate, capable of breaking the sulfur to sulfur cystine bonds within lower pH ranges, whereas the alkaline permanent wave compositions, having pHs in the range of about 7.5 to 9.5, require an alkaline salt of thioglycolic acid—so that the alkali can penetrate and swell the hair shaft for easier penetration of the reducing agent in order to break the sulfur to sulfur cystine bonds.

The use of diammonium dithiodiglycolate in acid or alkaline permanent wave lotions allows greater flexibility in processing time because it minimizes the possibility of overprocessing. This is due to the fact that the reaction of thioglycolic acid (TGA) with hair keratin is an equilibrium process. Thus by including diammonium dithiodiglycolate (oxidized TGA) in the wave lotion, the rate of the reaction of the thioglycolic acid with hair keratin is decreased and prevented from going to completion.

Generally, the permanent wave compositions of the prior art do not include moisturizers, such as glycerine, since moisturizers cause loss of curl, as disclosed in Cannell et al. U.S. Pat. No. 4,301,820.

One of the biggest problems associated with the permanent waving process is due to human error in the person applying the permanent waving lotion. If the reducing agent is applied to the hair shaft for the wrong period of time, too many or too few of the sulfur to sulfur bonds in the hair shaft are broken, resulting in seriously damaged hair or resulting in hair which has not been sufficiently treated to achieve a permanent wave with long lasting potential. Some of the reasons that the person applying the permanent wave composition has difficulty in determining the correct amount of time for processing is that the reducing agent reaction in breaking the sulfur to sulfur bonds is dependent upon the amount of heat applied to the hair; the amount of time the reducing agent is in contact with the hair; the concentration of reducing agent; the pH of the lotion applied; and the condition of hair.

Perhaps the most difficult factor for the applier of the permanent wave lotion to assess in determining how long to apply the reducing agent to the hair is the condition of the hair at the time of the permanent wave. It is well documented in the literature and prior art that the hair can be damaged by abuse of chemicals, e.g., by shampooing, permanent waving, tinting, frosting, bleaching, and particularly any hair treatment involving the use of hydrogen peroxide; mechanical treatment, e.g., thermal appliances; and environmental conditions, e.g., climate and pollution. It is well known that damaged hair, depending upon the stage and degree of damage of the hair, has significantly different chemical activity to reducing agents than normal or undamaged hair. If too many of the sulfur to sulfur bonds in the hair are broken by the reducing agent, the hair will be seriously weakened and may disintegrate.

It is theorized that somewhere in the range of about 20% to about 60% of the natural sulfur to sulfur cystine bonds in the hair shafts should be broken in order to give the hair the capability of being reshaped to any desired shape, such as curled around a rod or roller, and capable of retaining this shape. If too few of the sulfur to sulfur bonds are broken, the natural or normal configuration of the hair will predominate, causing the hair to retain its previous shape. This is because the predominant prior or natural bonds in the hair dictate that the hair will remain in the old configuration or shape. Hydrogen bonds are physically broken when wet hair is stretched and wrapped around a roller. When the hair is dried, the hydrogen bonds are reformed in a curled position or shape. While the hydrogen bonds aid to maintain the hair in the new configuration, the sulfur to sulfur cystine bonds are much stronger and, to a much greater extent than the hydrogen bonds, control the efficacy of the permanent wave.

In order to successfully provide a satisfactory permanent wave in the hair, the sulfur to sulfur cystine bonds reformed in the hair in the new or curled configuration, when the hair is later oxidized with the neutralizing agent, should be stronger than the prior or natural cystine hair bonds. It is desired, therefore, when permanent waving, that enough new bonds in a new hair configuration are formed during permanent waving to outweigh the number of old bonds remaining that tend to form the hair in its prior or natural configuration, whether it be straight or naturally curled.

Since damaged hair already has a significant number of the sulfur to sulfur cystine bonds broken due to some chemical, mechanical or environmental abuse, particularly the chemical abuses, such as bleaching, tinting or frosting, it is difficult to determine what length of time, and what reducing agent concentration to apply to the hair to provide the hair with the proper number of sulfur to sulfur bonds remaining after the reducing agent treatment. Significantly damaged hair, such as tinted hair, may require a reducing agent lotion application for a period of only about 5 minutes whereas a normal hair, not significantly damaged, may require the reducing agent lotion for a period of approximately 20 minutes under the same reducing agent concentration and temperature in order to result in both the damaged and normal hair having approximately the same curl configuration. Ideally, after the reducing agent treatment, every one of the hair shafts treated will contain the same ratio of broken to unbroken bonds so that this same ratio can be re-established in each hair shaft when the hair is in the new configuration to provide a consistent strong curl over the entire head of hair.

Generally, the reducing agent lotion is applied to the hair by first shampooing the hair and then applying the reducing agent lotion to the hair, either before or after the hair is wrapped around suitable rollers. Since it is not possible for even the experienced permanent wave applier to accurately determine visually the extent of damage to the hair in order to have a better idea of how long the reducing agent should be in contact with the hair, it is necessary to take a "test curl" so that after a predetermined amount of time, for example 10 minutes, a first roller is removed from the hair and the curl is felt and stretched in an attempt to determine if the curl formation is strong enough. Once it is determined that the reducing agent has been in contact with the hair for a sufficient time period, the hair is rinsed thoroughly with water while still on the rollers or rods and, while the hair remains on the rollers or rods, a neutralizing agent is applied to oxidize and reform the sulfur to sulfur bonds while the hair is in the new, rolled configuration. The neutralizing agent contains an oxidizing agent, such as hydrogen peroxide or a bromate salt, in order to reestablish the sulfur to sulfur bonds to leave the hair in a relatively permanent, e.g., 2–4 months, new configuration. The rods are removed, before or after rinsing out the neutralizing agent.

When the reducing agent lotion is applied to sections of the head prior to rolling that portion of the hair onto the rods it is called a lotion wrap whereas when the hair is rolled on the rods or rollers first and then the lotion applied onto all of the hair after rolling, this is called a water wrap. The timing for the reducing agent to be in contact with the hair for a lotion wrap is begun from the time that all rods are on the head, and the timing for a water wrap begins from the time that the lotion application is completed. The capability of using a water wrap is clearly more desirable since the lotion is applied to the entire head of hair all at once in a short period of time and can be rinsed from the hair all at once to provide a more uniform reducing agent contact time for all of the hair.

Other prior art patents directed to permanent waving compositions intended to permanently wave both normal and damaged hair are found in the Klemm et al. U.S. Pat. No. 4,273,143; and Cannel et al. U.S. Pat. No. 4,301,820. Japanese Patent No. 57-212110 appears to be directed to a post-permanent treatment containing glycerine to give hair sheen and luster.

Japanese published application No. 55-136857 teaches that cysteamine-based permanent waving compositions are more effective with thioglycolic acid reducing agents.

In accordance with the present invention, a cysteamine-based permanent wave composition, without a thioglycolate or thioglycolic acid, is provided in a single formula which can be applied in a single predetermined amount of time to the hair, regardless of the structure of the hair, whether it be damaged or not, and this composition is capable of being water wrapped or lotion wrapped without the use of a dryer, hair caps or other heat treatment to speed the reducing agent action.

Prior art alkaline compositions containing a salt of thioglycolic acid as a reducing agent are known to produce a tight curl but leave the hair feeling harsh due to the high alkalinity content. Prior art acid wave compositions containing glycerol monothioglycolate as a reducing agent require the mixing of the reducing agent into a separate lotion immediately prior to use since glycerol monothioglycolate will hydrolyze in contact with water and, therefore, must be kept separate until immediately prior to use. Further, the acid wave compositions generally require heat to help swell the hair for reaction with the reducing agent since the hair is not normally swelled sufficiently at the low pH of the acid wave compositions. The cysteamine-based reducing agent compositions of the prior art require the use of a compound selected from a monothioglycolate; a dithiodiglycolate; a monothioglycolic acid ester, e.g., glyceryl monothioglycolate; thioglycerol; a thiolactic acid; a sulfite, a hyposulfite, or a bisulfite. The cysteamine-based reducing agent-containing permanent wave compositions of the present invention solve the above mentioned prior art deficiencies without containing any substantial amount, and preferably without any, of a monothioglycolate; a dithiodiglycolate; a monothioglycolic acid ester, e.g., thioglycerol; a thiolactic acid; a sulfite; a hyposulfite, a hyposulfite, or a bisulfite.

SUMMARY OF THE INVENTION

In brief, the present invention is directed to a single formula, mild permanent wave reducing composition and method of permanently waving or reshaping human hair that provides a strong, long lasting curl and leaves the hair soft while minimizing further damage to already damaged hair. Generally, the composition contains a cysteamine reducing agent compound selected from the group consisting of cysteamine, a cysteamine salt, and mixtures thereof; preferably alone (without a monothioglycolate; a monothioglycolic acid ester, e.g., thioglycerol; a thiolactic acid; a sulfite; a hyposulfite, or a bisulfite second reducing agent). The cysteamine compound should be present in an amount of about 7.8% to about 9.0%, preferably about 7.8% to about 8.5% by weight; and sufficient additional alkali, if necessary, to bring the pH of the composition to about 7.8 to about 8.5. Optionally, a hair softening and/or moisturizing agent, such as glycerine is included in the composition in an amount of about 0.1% to about 20% by weight, preferably about 0.1% to about 15% by weight of the composition. This composition is easy to use and apply without the use of a monothioglycolate; a dithioglycolate; a monothioglycolic acid ester, e.g., thioglycerol; a thiolactic acid; a sulfite; a hyposulfite, or a bisulfite and without damaging the hair while providing a strong, tight curl and leaving the hair unexpectedly soft. The composition can be lotion or water wrapped and can be used with or without heat. Unexpectedly, the composition is applied to any type of hair, regardless of structural damage to the hair, resulting in the same degree of curl tightness and softness and can be applied much more frequently than prior art permanent wave compositions without significant damage to the hair.

Accordingly, an aspect of the present invention is to provide a new and improved permanent wave composition capable of breaking sulfur to sulfur bonds in human hair so that the hair can be reconfigured in a different configuration. The sulfur to sulfur human hair bonds can be reestablished with an oxidizing agent to maintain the new hair configuration for a substantial time period.

Another aspect of the present invention is to provide a new and improved permanent wave lotion containing a reducing agent capable of breaking sulfur to sulfur hair bonds without causing further significant damage to tinted, frosted, bleached or other substantially damaged hair.

Another aspect of the present invention is to provide a new and improved cysteamine-based permanent wave reducing agent composition that includes essentially no monothioglycolate; dithiodiglycolate; monothioglycolic acid ester, e.g., thioglycerol; thiolactic acid; sulfite; hyposulfite, or bisulfite that is capable of breaking sulfur to sulfur human hair bonds leaving normal and damaged hair with approximately the same ratio of broken to unbroken sulfur to sulfur bonds when contacted with the composition for the same time period so that the same degree of curl tightness can be achieved in both normal and damaged hair.

Another aspect of the present invention is to provide a permanent wave reducing agent-containing composition including a hair softening and moisturizing agent that enhances the curl achieved with the composition.

These and other objects and advantages of the present invention will become apparent from the following detailed description of the preferred embodiment.

DETAILED DESCRIPTION OF THE PREFERRED EMBODIMENT

Figure 1:
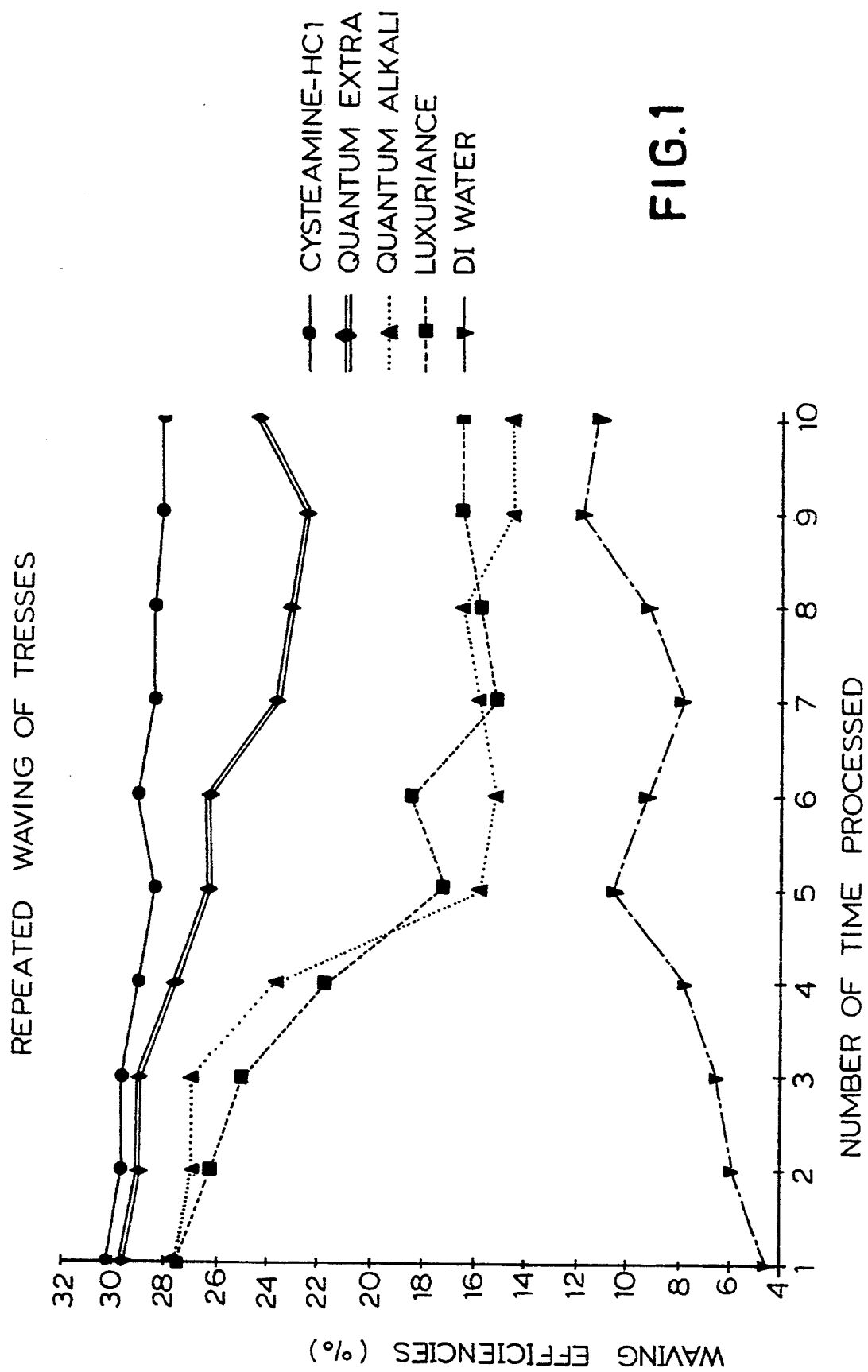
FIG. 1 is a graph showing the waving efficiencies of a number of waving lotions versus number of times the hair was processed with each waving lotion.

The present invention is directed to a permanent wave composition capable of permanently waving both damaged and undamaged hair in a single formulation, water-wrap, applied for a constant processing time as a mild permanent that produces a tight, long lasting curl formation and can be applied frequently without significant hair damage. The capability of permanently waving both damaged and undamaged hair repeatedly with a single formulation in a single processing time without requiring a test curl, without causing further damage to the hair, is totally unique in the industry and removes all room for error from the person applying the permanent wave lotion.

The composition of the present invention is a single formula, mild, alkaline permanent wave conditioning composition capable of waving or reshaping human hair and provides a strong, long lasting curl without further damaging already damaged hair. Generally, the composition contains a cysteamine compound selected from the group consisting of cysteamine, a cysteamine salt, and mixtures in an amount of about 7.8% by weight to about 9.0% by weight, particularly about 8% to about 8.6% by weight. In another embodiment, the reducing agent composition has a pH in the range of about 7.8 to about 8.5, and particularly about 8.0 to about 8.3. Preferably, the reducing composition also includes a hair moisturizer and/or softener selected from a polyhydroxyl alkyl compound, a polyalkylene glycol glycerol ether, an ethoxylated fatty alcohol, a fatty alcohol polymerized ether, and mixtures thereof in an amount of about 0.1% to about 20% by weight, particularly about 0.1% to about 15% by weight.

Optionally, the composition of the present invention includes a conditioner to improve the combing and manageability of the hair. Particularly, suitable conditions are the polymeric quaternary ammonium salts, such as Polyquaternium 1 through Polyquaternium 14, inclusive, conditioners defined on page 245, CTFA Cosmetic Ingredient Dictionary, Third Edition, 1982, hereby incorporated by reference. The preferred conditioners are Polyquaternium-4, Polyquaternium-10 and Polyquaternium-11. The conditioner, when added, is included in an amount of about 0.01% to about 2.0% by weight of the composition.

Other common cosmetic additives can be incorporated into the composition of the present invention, as long as the basic properties of the permanent wave composition are not substantially adversely affected. These additives include, but are not limited to, commonly used fragrances, dyes, opacifiers, pearlescing agents, thickeners, foam stabilizers, preservatives, water softening agents, acids, bases, buffers and the like; and will usually be present in weight percentages of less than about 1% each, and about 2% to about 5% in total. The composition vehicle is predominantly water but organic solvents also can be added to the composition in order to solubilize compounds that are not sufficiently soluble in water. Suitable solvents include the lower alcohols, such as ethanol and isopropanol and mixtures. These solvents can be present in the hair setting composition of the present invention in an amount from about 1% to about 75% by weight and in particular from about 5% to about 50% by weight, based on the total weight of the composition.

The composition optionally can be thickened, for example, with sodium alginate, gum arabic, cellulose derivatives such as methylcellulose, hydroxyethylcellulose, hydroxypropylmethylcellulose and carboxymethylcellulose, and various polymeric thickeners, such as acrylic acid derivatives. It is also possible to use inorganic thickeners, such as bentonite. These thickeners, when included, preferably are present in an amount from about 0.1% to about 10% by weight and, in particular, from about 0.5% to about 3% by weight, based on the total weight of the composition.

The composition has the pH in the range of about 7.8 to about 8.5. To achieve the full advantage of the present invention, the composition has a pH of about 8.0 to 8.3 for best curl retention when cold waved. This pH can be achieved by the addition of an alkanolamine, ammonia, an ammonium carbonate, or a metal hydroxide to the composition of the present invention.

Moisturizers enhance the curl formation of the permanent wave composition of the present invention. The use of polyhydric alcohols or polyhydroxy alkane compounds, such as ethylene glycol, glycerine, propylene glycol, or polyoxyethylene glyceryl ether in this composition leave the hair in better condition due to humectant properties and surprisingly does not compromise curl formation, but provides the hair with a more uniform and natural curl.

These moisturizers are selected from the group consisting of polyhydroxyalkyl compounds, particularly alkylene glycols and polyalkylene glycols, and especially ethylene glycol and the polyethylene glycols; propylene glycol and the polypropylene glycols; polyethylene glycol glyceryl ethers; ethoxylated fatty alcohols; and fatty alcohol polyglycol ethers. Examples of suitable moisturizers include glycols and triols such as glycerine, ethylene glycol, propylene glycol, 1,3-butylene glycol, 1,2,6-hexanetriol, 1,5-pentanediol, 2-methyl pentanediol-2,4, and 2-ethyl hexanediol-1,3. Further examples of suitable moisturizers include the polyalkylene glycols, such as those compounds having the formula

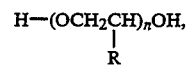

wherein R is H or $CH_3$, and n has an average value of 2 to 600; when R=H, particularly suitable moisturizers have n in the range of 4 to 600; and when R=$CH_3$, particularly suitable moisturizers have n in the range of 2 to 34. The polyalkylene glycols that can be used as moisturizers in the permanent wave composition of the present invention are exemplified by, but not limited to, compounds such as polyethylene glycol 200; polyethylene glycol 400; polyethylene glycol 600; polypropylene glycol 150; tetraethylene glycol; and dipropylene glycol.

Examples of other suitable moisturizers include the polyethylene glycol glyceryl ethers, such as polyethylene glycol 600 glyceryl ether and polyethylene glycol 26 glyceryl ether. Furthermore, the ethoxylated nonyl phenols and ethoxylated octyl phenols, particularly nonoxynol, $C_9H_{19}C_6H_4(OCH_2CH_2)_n$—OH, wherein n averages at least 6 and up to about 100; and octoxynol, $C_8H_{17}S_6H_4(OCH_2CH_2)_n$—OH, wherein n averages at least 7 and up to about 40, also are suitable moisturizers for use in the composition of the present invention. Suitable ethoxylated fatty alcohols for use as moisturizers in the composition of the present invention include compounds having the formula R—$(OCH_2CH_2)_n$OH, wherein R is an alkyl group containing from about 12 to about 30 carbon atoms and n averages at least 6. In addition, fatty alcohol polyglycol ethers having the formula

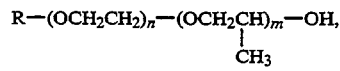

wherein R is an alkyl group containing from about 8 to about 18 carbon atoms, n=0 to 6, m=0 to 6, and n+m is at least 6, also are useful as moisturizers in the composition of the present invention.

The composition of the present invention is easy to use and apply, repeatedly, without damaging the hair while providing a strong, tight curl and leaving the hair unexpectedly soft. The composition can be lotion or water wrapped and can be used with or without heat. Unexpectedly, the composition is applied to any type of hair, regardless of structure damage to the hair, resulting in the same degree of curl tightness and softness.

It is most surprising in the art that the composition of the present invention is capable of treating both normal and damaged hair, particularly tinted hair and bleached hair, in a single formula, using a non-critical processing time for both normal and damaged hair and requires neither a test curl to determine the processing time nor a dryer to fix the processing time while capable of repeated applications without significant hair damage.

The cysteamine-based waving lotion composition of the present invention was compared to other common reducing agents including: ammonium thioglycolate (ATG), glycerylmonothioglycolate (GMT), cysteine and dithiotreitol. To determine waving efficiency, the tresses were subjected to a curl waving procedure described hereinafter keeping the pH constant and varying the concentration of the active ingredient. In a second series of experiments the concentration was kept constant and the pH was varied. Under similar. experimental conditions, hair damage was measured using "aggressivity factor" and also using a new technique called Mercury tagging whereby hair reduction is measured by tagging the reduced sites of the hair and photographing the cross sections under electron microscopy (SEM). The results of these tests are shown below.

In the "aggressivity factor" test, it can be seen that with ATG and GMT at a constant concentration, when pH is varied, the aggressivity factor gets bigger versus time indicating that the damage done to the hair is progressively worse. Similarly, when the pH is kept constant and the concentration is varied, hair damage gets progressively worse.

With cysteamine, it was found that the aggressivity factor leveled off within a relatively narrow pH or concentration range and was not as linear as the other reducing agents, indicating that damage to the hair does not get worse when hair is exposed to increasing concentrations or pH of the waving lotion. The cysteamine wave lotion used was not buffered and did not have any stop action ingredients.

These findings were confirmed via SEM pictures where the number of reduced sites on the hair fiber were tagged. With ATG and GMT, increasing the pH or concentration increased the number of reduced sites but with cysteamine, there was substantially little or no change with increased pH or concentration.

Waving efficiencies were determined keeping the pH constant and varying the concentration and also keeping the concentration constant and varying the pH. The waving efficiency of ATG and GMT was a function of pH and concentration. However, with cysteamine, the waving efficiency increased with pH only up to a pH of 8.0. Between 8.0 and 9.0 the waving efficiency of cysteamine was relatively constant. Similarly, within the molar concentrations of 0.60 to 0.80, the waving efficiencies of cysteamine were constant and did not increase.

These unexpected findings, with cysteamine, namely constant performance over a relatively narrow pH and concentration range, led to the discovery of further benefits for cysteamine. With conventional waving agents, it is well known in the art to change the concentration and/or pH when waving hair with different degrees of damage. For example, when preparing a formula for bleached hair, formulators will lower the aggressiveness of the active ingredient by lowering its pH or concentration. Since the performance of cysteamine did not change over the narrow pH and concentration range, further experiments were performed using the same formula (without changing concentration or pH) using normal hair (relatively undamaged) and bleached hair (hair bleached with a mixture of ammonium persulfate, alkaline salts and 20 volume percent hydrogen peroxide having a higher degree of damage percent). Again, surprisingly, it was found that the same formula containing 0.73 molar concentration of cysteamine, at a pH of 8.4, waves normal, tinted and bleached hair without causing excessive damage to bleached hair.

The next series of experiments was done to determine if hair could be repeatedly permed with cysteamine and to measure the effect on curl formation and damage. To determine the effect of multiple waving on hair tresses, a set of hair swatches was repeatedly waved (10 times) using cysteamine, ATG, GMT and water (as control). As seen in the FIG. 1 graph, the waving efficiency of conventional reducing agents decreases with repeated perms, as expected. However, with cysteamine, the waving efficiencies were relatively unaffected even after penning hair 10 times.

The results of this test were further confirmed on growing hair in a salon. A group of 13 experimental clients was permed with cysteamine and a second group of 11 experimental clients were treated with a leading acid perm. All clients were permed twice with only 6 weeks between the two perm treatments. After the second perm, the clients' hair was graded by licensed cosmetologists. Hair breakage was graded on a scale of 1–5 (1 lowest, 5 highest). In the group that was penned with the acid perm, 5 out of 11 clients showed some degree of breakage and the average breakage was rated at 0.55. In the cysteamine waved group, one model out of 13 showed any breakage, and the average breakage was rated as 0.04. These differences were calculated to be significant at the 98% confidence level.

Figure 2:
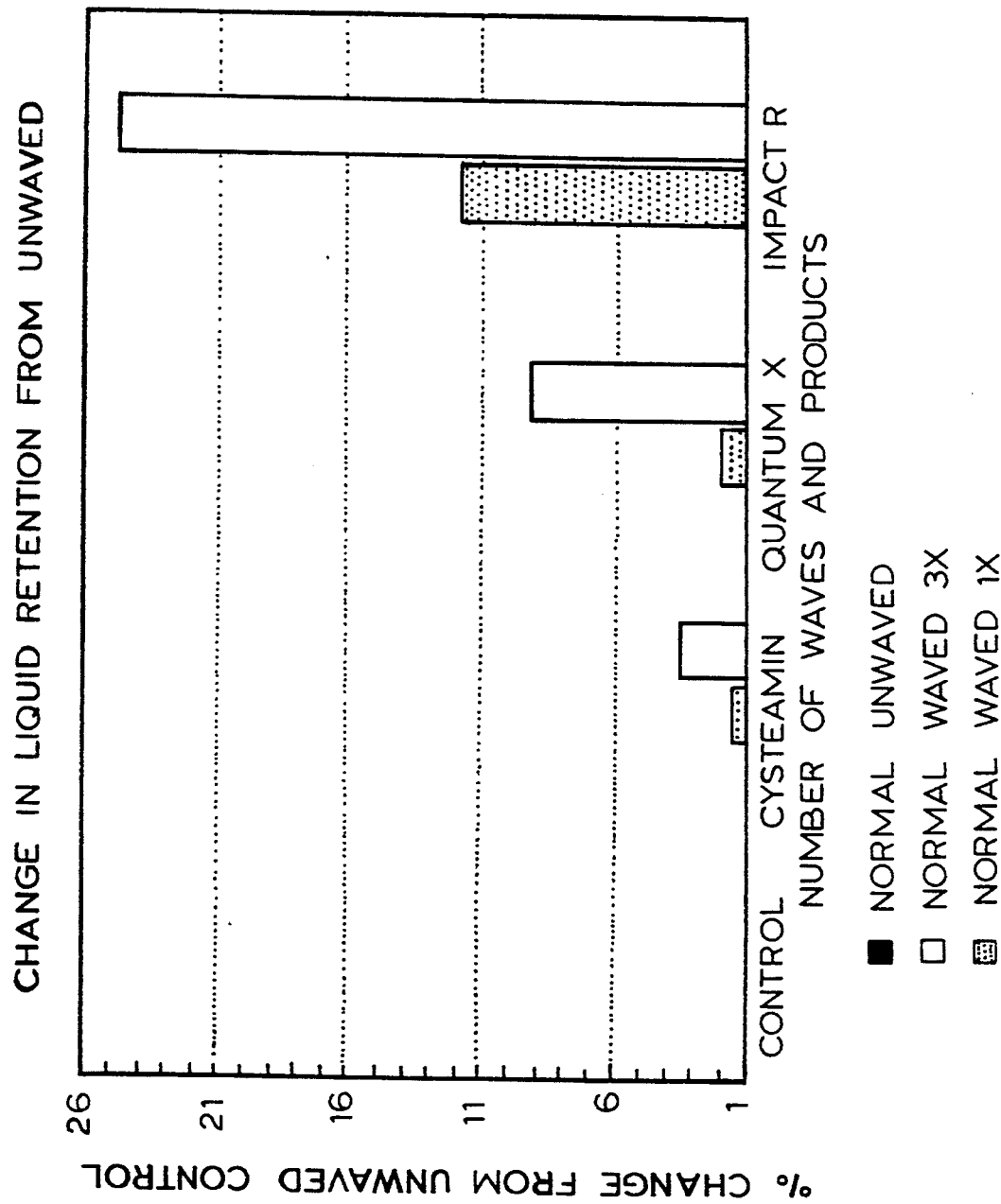
FIG. 2 is a graph showing the liquid retention of normal hair waved one time compared to the same hair waved three times with various waving lotions to determine the percent change in liquid retention.
Figure 3:
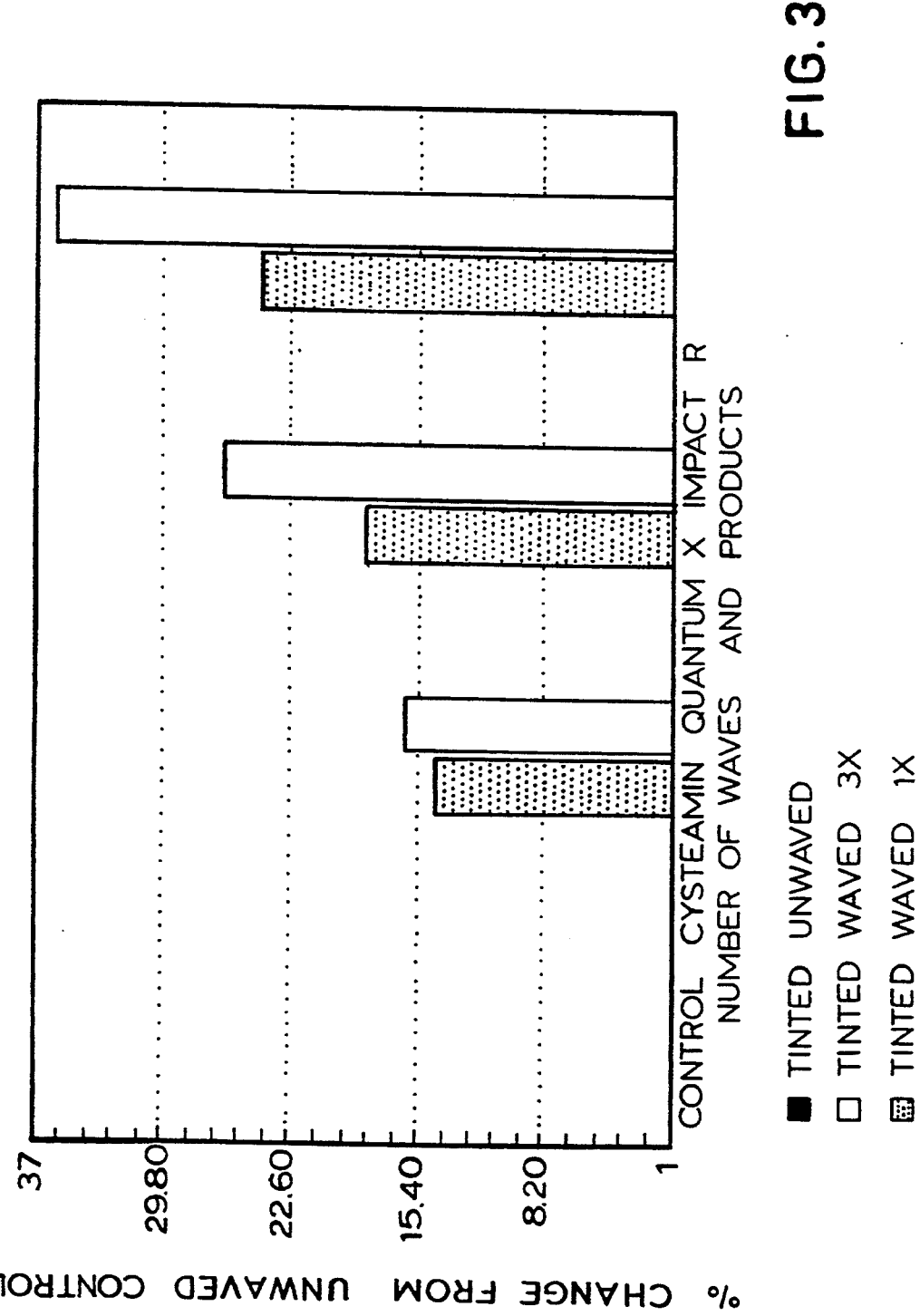
FIG. 3 is a graph, similar to FIG. 2, showing the liquid retention of tinted hair waved one time compared to the same hair waved three times, with various waving lotions, to determine the percent change in liquid retention.

Hair damage was also measured analytically in the laboratory by a technique called Liquid Retention. The principle involved in the Liquid Retention test is based on the fact that damaged hair becomes more porous and absorbs more moisture. The greater the amount of moisture picked up by the hair, the greater the damage. Moisture pick up (Liquid Retention) was measured on hair that was waved once or three times with cysteamine; a leading acid wave; and a leading alkaline wave. As can be seen in the FIG. 2 graph, there was no significant increase in the amount of moisture picked up by hair which was waved one time and three times with cysteamine. However, with the acid and alkaline waved hair, the moisture pick up after three wavings was significantly greater than one time waved hair. Similar results were obtained on tinted hair, as shown in the graph of FIG. 3.

Without being bound to any particular theory, cysteamine, within the concentration and pH ranges shown below, has some unexpected properties, namely, minimal damage and good curl efficacy. This may be attributed to the amine functionality of the molecule.

| FORMULATION | % W/W |
|---|---|
| Cysteamine HCl | 7.8–9.0 |
| Ammonium Hydroxide | q.s. to pH 7.8–8.8 |
| Nonoxynol-15 | 0.90 |
| (Igepal CO-730) | |
| (fragrance solubilizer) | |
| Fragrance | 0.30 |
| Water | q.s. to 100 |

When cysteamine HCl is used below 7.8% w/w active, the product performance measured as curl efficacy is not adequate and above 9.0 w/w the product, while it performs well, becomes too irritating to the skin. Similarly, below pH 7.8 cysteamine performance is not adequate and at a pH beyond 8.8, the composition is too irritating to the skin. The new and unexpected results described herein are only obtained within this narrow range of concentration and pH. Many modifications and variations of the invention as hereinbefore set forth can be made without departing from the spirit and scope thereof and, therefore, only such limitations should be imposed as are indicated by the appended claims.

What is claimed is:

1. A method of breaking sulfur to sulfur bonds in human hair to leave the hair weakened so that it can be reconfigured to a predetermined configuration, while minimizing further damage to damaged hair, including contacting the hair for a predetermined amount of time with an aqueous cysteamine reducing agent-containing composition comprising about 7.8% to about 9.0% by weight of a cysteamine; and sufficient alkali such that the composition has a pH of about 7.8 to about 8.8; forming the hair in a desired configuration such that the hair is in contact with the reducing agent-containing composition while formed in the new configuration; and then removing most of the reducing agent-containing composition from the hair.

2. The method of claim 1 further including wrapping a plurality of human hair sections around a plurality of mandrels to reconfigure the hair sections in a plurality of curl configurations such that the hair is curl-configured while in contact with the reducing agent-containing composition; and removing the mandrels sequentially after said predetermined time period without testing the hair from one of the first removed mandrels for curl tightness.

3. The method of claim 1, wherein the composition includes a polyhydric moisturizer in an amount of about 0.1% to about 20% by weight of the composition.

4. The method of claim 3, wherein the polyhydric moisturizer is selected from the group consisting of polyhydroxyalkyl compounds; polyalkylene glycols; glyceryl ether compounds; ethoxylated fatty alcohols; ethoxylated alkyl phenols; and fatty alcohol polyglycol ether compounds; or mixtures thereof.

5. The method of claim 1, wherein the cysteamine is included in an amount of about 8.0% to about 8.3% by weight of the composition.

6. The method of claim 1, wherein the hair is contacted with the aqueous cysteamine reducing agent-containing composition prior to forming the hair in the desired configuration.

7. The method of claim 1, wherein the hair is contacted with the aqueous cysteamine reducing agent-containing composition after the hair is formed in the desired configuration.

8. The method of claim 1 further including the step of shampooing the hair prior to contacting the hair with the aqueous cysteamine reducing agent-containing composition.

9. The method of claim 1, wherein most of the reducing agent-containing composition is removed by rinsing with water.

10. A method of permanently waving hair comprising the steps of contacting the hair with an aqueous cysteamine reducing agent-containing composition comprising about 7.8% to about 9.0% by weight of a cysteamine; and sufficient alkali such that the composition has a pH of about 7.8 to about 8.8 to break sulfur to sulfur bonds in the hair; forming the hair in a desired configuration such that the hair is in contact with the reducing agent-containing composition while formed in the new configuration; removing most of the reducing agent-containing composition from the hair; and then oxidizing the configured hair to reform sulfur to sulfur hair bonds.

11. The method of claim 1 further including wrapping a plurality of human hair sections around a plurality of mandrels to reconfigure the hair sections in a plurality of curl configurations such that the hair is curl-configured while in contact with the reducing agent-containing composition; contacting the configured hair sections with an oxidizing agent-containing composition, while the hair sections are in the plurality of curl configurations, and then rinsing the hair and removing the mandrels.

12. The method of claim 5, wherein the aqueous cysteamine reducing agent-containing composition and the oxidizing agent-containing compositions are applied without testing the hair, from one of the first removed mandrels, for curl tightness.

13. The method of claim 6, wherein the oxidizing agent-containing composition is rinsed from the hair before removing any mandrels from the hair.

14. The method of claim 10, wherein the oxidizing agent-containing composition is rinsed from the hair after removing the mandrels from the hair.

15. The method of claim 10, wherein the hair is contacted with the aqueous cysteamine reducing agent-containing composition prior to forming the hair in the desired configuration.

16. The method of claim 10, wherein the hair is contacted with the aqueous cysteamine reducing agent-containing composition after the hair is formed in the desired configuration.

17. The method of claim 10 further including the step of shampooing the hair prior to contacting the hair with the aqueous cysteamine reducing agent-containing composition.

18. The method of claim 10, wherein most of the reducing agent-containing composition is removed by rinsing with water.

19. The method of claim 10, wherein the cysteamine reducing agent-containing composition includes a polyhydric moisturizer in an amount of about 0.1% to about 20% by weight of the composition.

20. The method of claim 19, wherein the polyhydric moisturizer is selected from the group consisting of polyhydroxyalkyl compounds; polyalkylene glycols; glyceryl ether compounds; ethoxylated fatty alcohols; ethoxylated alkyl phenols; and fatty alcohol polyglycol ether compounds; or mixtures thereof.

21. The method of claim 10 wherein the cysteamine is included in the reducing agent-containing composition in an amount of about 8.0% to about 8.3% by weight of the composition.

* * * * *

UNITED STATES PATENT AND TRADEMARK OFFICE
CERTIFICATE OF CORRECTION

PATENT NO. : 5,382,426

DATED : JANUARY 17, 1995

INVENTORS : ARUN NANDAGIRI, ET AL.

It is certified that error appears in the above-identified patent and that said Letters Patent is hereby corrected as shown below:

Column 1, line 8, after "Jan. 10," delete "1934" and substitute therefor -- 1992 --.

Signed and Sealed this

Twenty-first Day of March, 1995

Attest:

BRUCE LEHMAN

Attesting Officer    Commissioner of Patents and Trademarks